United States Patent [19]
Wang et al.

[11] Patent Number: 4,879,212
[45] **Date of Patent: * Nov. 7, 1989**

[54] PEPTIDE COMPOSITION AND METHOD FOR THE DETECTION OF ANTIBODIES TO HTLV-III

[75] Inventors: Chang Y. Wang, Great Neck; James J. G. Wang, Flushing, both of N.Y.

[73] Assignee: United Biomedical Inc., Lake Success, N.Y.

[ * ] Notice: The portion of the term of this patent subsequent to Apr. 5, 2005 has been disclaimed.

[21] Appl. No.: 13,014

[22] Filed: Feb. 10, 1987

Related U.S. Application Data

[63] Continuation-in-part of Ser. No. 847,102, Apr. 2, 1986, Pat. No. 4,735,896, which is a continuation-in-part of Ser. No. 837,566, Mar. 4, 1986, abandoned, which is a continuation-in-part of Ser. No. 774,644, Sep. 11, 1985, abandoned.

[51] Int. Cl.[4] ........................ C12Q 1/70; G01N 33/53
[52] U.S. Cl. ........................................ 435/5; 530/324; 530/325; 530/326; 530/327; 435/7; 436/811; 422/61
[58] Field of Search ................ 435/5, 7; 530/324–327; 436/811; 422/61

[56] References Cited

U.S. PATENT DOCUMENTS 4,554,101 11/1985 Hopp ............................ 436/543 X
4,629,783 12/1986 Cosand ............................... 530/324

FOREIGN PATENT DOCUMENTS 0201716 11/1986 European Pat. Off. ................ 435/5
WO8404372 11/1984 PCT Int'l Appl. .
WO8601834 3/1986 PCT Int'l Appl. .
86/06414 11/1986 PCT Int'l Appl. ..................... 435/5

OTHER PUBLICATIONS

Coffin et al., *Nature* 321, p. 10 (May 1986).
Jungkind et al., "Effect of Using Heat-Inactivated Serum with the Abbott Human T-Cell Lymphotropic Virus Type III Antibody Test", J. Clin. Microbiol. 23:381-382 (Feb. 1986).
Chang et al., "Detection of Antibodies to Human T--Cell Lymphotropic Virus-III (HTLV-III) with an Immunoassay Employing a Recombinant *Escherichia coli*-Derived Viral Antigenic Peptide", Bio/Technology 3:905-909 (Oct. 1985).
Veronese etal., "Characterization of gp41 as the Transmembrane Protein Coded by the HTLV-III/LAV Envelope Gene", Science 229:1402-1405 (Sep. 27, 1985).
Robey et al., "Characterization of Envelope and Core Structural Gene Products of HTLV-III with Sera from AIDS Patients", Science 228:593-595 (May 3, 1985).
Crowl et al., "HTLV-III env Gene Products Synthesized in *E. coli* are Recognized by Antibodies Present in the Sera of AIDS Patients", Cell 41:979-986 (Jul. 1985).
Schneider et al., "A Glycopolypeptide (gp 100) is the Main Antigen Detected by HTLV-III Antisera", Med. Microbiol. Immunol. 174:35-42 (1985).
Schupbach et al., "Antibodies to HTLV-III in Swiss Patients with AIDS and Pre-AIDS and in Groups at Risk for AIDS", N. Engl. J. Med. 312:265-270 (Jan. 31, 1985).
Wang et al., "Detection of Antibodies to Human T-Lymphotropic Virus Type III by Using a Synthetic Peptide of 21 Amino Acid Residues Corresponding to a Highly Antigenic Segment of gp41 Envelope Protein", Proc. Natl. Acad. Sci. U.S.A. 83:6159-6163 (Aug. 1986).
Schneider et al., "Shedding and Interspecies Type Sero-Reactivity of the Envelope Glycopolypeptide gp120 of the Human Immunodeficiency Virus", J. Gen. Virol. 67:2533-2538 (1986).
Chanh et al., "Induction of Anti-HIV Neutralizing Antibodies by Synthetic Peptides", EMBO J. 5:3065-3071 (Nov. 1986).
Matthews et al., "Restricted Neutralization of Divergent Human T-Lymphotropic Virus Type III Isolates by Antibodies to the Major Envelope Glycoprotein", Proc. Natl. Acad. Sci. U.S.A. 83:9709-9713 (Dec. 1986).
Lange et al., "Distinct IgG Recognition Patterns During Progression of Subclinical and Clinical Infection with Lyphadenopathy Associated Virus/Human T Lyphotropic Virus", Br. Med. J. 292:228-230 (Jan. 25, 1986).
Pert et al., "Octapeptides Deduced from the Neuropeptide Receptor-Like Pattern of Antigen T4 in Brain Potently Inhibit Human Immunodeficiency Virus Receptor Binding and T-Cell Infectivity", Proc. Natl. Acad. Sci. U.S.A. 83:9254-9258 (Dec. 1986).

(List continued on next page.)

*Primary Examiner*—Christine M. Nucker
*Attorney, Agent, or Firm*—Morgan & Finnegan

[57] ABSTRACT

The present invention relates to a method for.the detection and diagnosis of AIDS (acquired immune deficiency syndrome) ARC (AIDS Related Complex) and pre-AIDS conditions in body fluids by the use of a chemically synthesized peptide composition. The detection method includes an enzyme-linked immunosorbent assay (ELISA), an immunoradiometric assay (IRMA), and other forms of immuno assay procedures such as enzyme immuno blotting assay on nitrocellulose paper and hemagglutination assay using the peptide composition as the antigen. The preferred detection method is ELISA.

The present invention also relates to a vaccine and a method for generating antibodies to HTLV-III in healthy mammals, including humans by the use of the chemically synthesized peptide composition.

52 Claims, No Drawings

OTHER PUBLICATIONS

Certa et al., "Subregions of a Conserved Part of the HIV gp41 Transmembrane Protein are Differentially Recognized by Antibodies of Infected Individuals", EMBO J. 5:3051-3056 (Nov. 1986).

Robey et al., "Prospect for Prevention of Human Immunodeficiency Virus Infection: Purified 120-kDa Envelope Glycoprotein Induces Neutralizing Antibody", Proc. Natl. Acad. Sci. U.S.A. 83:7023-7027 (Sep. 1986).

Chanh et al., "Human Immunodeficiency Virus gp120 Glycoprotein Detected by a Monoclonal Antibody to a Synthetic Peptide", Eur. J. Immunol. 16:1465-1468 (1986).

Starcich et al., "Identification and Characterization of Conserved and Variable Regions in the Envelope Gene of HTLV-III/LAV, the Retrovirus of AIDS", Cell 45;637-648 (Jun. 6, 1986).

Kanner et al., "Human Retroviral env and gag Polypeptides: Serologic Assays to Measure Infection", J. Immunol. 137:674-678 (Jul. 15, 1986).

Chassagne et al., "A Monoclonal Antibody Against LAV gag Precursor: Use for Viral Protein Analysis and Antigenic Expression in Infected Cells", J. Immunol. 136:1442-1445 (Feb. 15, 1986).

Chang et al., *Nature,* vol. 315, pp. 151-154 (May 9, 1985).

Pauletti et al., *Anal. Biochem.,* 151, 540-546 (1985).

PEPTIDE COMPOSITION AND METHOD FOR THE DETECTION OF ANTIBODIES TO HTLV-III

CROSS REFERENCE TO RELATED APPLICATIONS

This is a continuation-in-part application of Application Ser. No. 847,102 filed Apr. 2, 1986, now U.S. Pat. No. 4,735,896, which is in turn a continuation-in-part application of Application Ser. No. 837,566 filed Mar. 4, 1986, abandoned, which is in turn a continuation-in-part application of Application Ser. No. 774,644, filed Sept. 11, 1985, abandoned.

In 1986, the members of a subcommittee empowered by the International Committee on The Taxonomy of Viruses proposed human immunodeficiency virus, abbreviated as HIV, as an appropriate name for the retrovirus isolates as the causative agents for AIDS. The proposal was adopted in 1986.

INTRODUCTION

The present invention relates to a peptide composition and a highly sensitive, accurate and reliable method for the detection of antibodies to HTLV-III in body fluids, for the diagnosis of AIDS (acquired immune deficiency syndrome) ARC (AIDS Related Complex) and pre-AIDS conditions. The peptide composition is also useful as a vaccine for AIDS, ARC or pre-AIDS conditions by stimulating the production of antibodies to HTLV-III to provide protection against infection by HTLV-III or LAV in healthy mammals, including humans. The peptide composition comprises a synthetic peptide having about thirty five amino acids and a mixture of peptides. The amino acid sequence of the peptide and each of the peptides useful in the peptide compositions is chemically synthesized to correspond to segments of the envelope protein, p41, and a segment of the gag protein, p24, of HTLV-III. The peptide composition of the present invention has been found to be highly immunoreactive with antibodies in sera of patients with AIDS, ARC and pre-AIDS conditions.

More specifically, the present invention is directed to the use of a peptide composition comprising a peptide or a mixture of chemically synthesized peptides, one peptide containing therein a segment of about thirty five (35) amino acids (hereinafter referred to as the 35mer peptide), one peptide containing therein a segment of about twenty-one (21) amino acids (hereinafter referred to as the 21mer peptide), a third containing therein a segment of nineteen (19) amino acids (hereinafter referred as the 19mer peptide), and a fourth peptide containing therein a segment of eleven (11) amino acids (hereinafter referred to as the 11mer peptide) in a prescribed sequence. The 35mer peptide or a mixture of the 21mer peptide, the 19mer peptides and optionally the 11mer peptide are useful for the detection of antibodies to the HTLV-III virus in human body fluids of AIDS, ARC or pre-AIDS patients. The amino acids herein mentioned includes substitutions by analogous acids of the prescribed amino acids, as long as the immunogenic structure of the peptides are preserved.

The detection methods include an enzyme-linked immunosorbent assay (ELISA), an immunoradiometric assay (IRMA) and other methods of immuno assay procedures such as enzyme immunoblotting on nitrocellulose paper and hemagglutination using the peptide composition as the antigen. The preferred detection method is by ELISA.

BACKGROUND OF THE INVENTION

Acquired immune deficiency syndrome (AIDS) has been recently recognized in several countries. Due to its devastating effect on the patients and indications that the disease is spreading, much effort has been devoted to elucidate and identify the cause of the disease. Epidemiologic data suggests that AIDS is caused by an infectious agent that is horizontally transmitted by intimate contact or exposure to blood or certain blood products.

In 1983, F. Barre-Sinoussi et al. of the Institute Pasteur reported the isolation of a T-lymphotropic retrovirus from a patient at risk for AIDS. The retrovirus appeared to be a member of the human T-cell leukemia virus (HTLV) family. However, its immunological response is distinct from known HTLV-I or HTLV-II. F. Barre-Sinoussi et al., *Science,* 220, pp. 868 (May, 1983).

A similar virus, designated HTLV-III, has also been isolated by R. C. Gallo's group at National Cancer Institute from the blood samples of a large number of AIDS and ARC patients by co-cultivation with a permissive T-cell line H9. See Popovic, M. et al., *Science,* 224, pp. 497 (1984) and Gallo, R. et al., *Science,* 224, pp. 500 (1984).

V. S. Kalyanaraman et al. of the Center for Disease Control, Atlanta, Georgia, reported the isolation of a lymphadenopathy associated virus (LAV) in patients with AIDS and the development of a radioimmunoprecipitation assay using the major core protein, p25, of LAV. Their test procedure involved the use of the LAV virus propagated in primary cultures of blood lymphocytes and harvested. The p25 core protein was isolated from the harvested virus, labelled with $I^{125}$ and used as a target antigen. The labelled antigen was added to serum and precipitation of at least 15% of the labelled antigen is regarded as a positive result. See V.S. Kalyanaraman et al., *Science,* 225, pp. 321 (July 1984). However, based on the reported results, the test was positive only for 41% of the AIDS patients and 72% positive for patients with lymphadenopathy syndrome (LAS) otherwise known as ARC. This means that the procedure is not sufficiently sensitive or accurate to be used as a detection or diagnostic tool for screening serum for the presence of antibodies to the AIDS virus.

LAV and HTLV-III, as well as various strains of related retrovirus isolated from AIDS patients share several important characteristics. See Feorino, P. et al., *Science,* 225, pp. 69 (1984); Levy, J. et al., *Science,* 225, pp. 840 (1984). These include viral repolication in OKT4+human T-cell leukocytes, in vivo and in vitro; association with impaired T-cell proliferation, the appearance of cytopathic effects; (See Montagnier et al., *Human T Cell Leukemia Virus,* pp. 363, Cold Spring Harbor Laboratory, 1984; Popovic, M. et al., op. cit., and Klatzmann, D. et al. *Science,* 225, pp. 59 (1984)) and recognition by antibodies in the sera of AIDS and ARC patients. See Montagnier, et al., op. cit.; Levy J. et al., op. cit., Sarngadharan, M. et al., *Science,* 224, pp. 505 (1984); Safai, B. et al., *Lancet, i,* pp. 1438 (1984); Brun-Vezinet, F., et al., *Lancet, i,* pp. 1253 (1984); Brun Vezinet, F. et al., *Science,* 226, pp. 453 (1984); Goldbert, J. et al., *Lancet, ii,* pp. 711 (1984) and Laurence J. et al., *New England J. Med.,* 311, pp. 1269 (Nov. 1984).

In November 1984, L. W. Kitchen et al. reported the use of a HTLV-III infected line, designated H9/HTLV-III, to test the incidents of AIDS in haemophiliac patients. The method involved inactivation of the virus with 2% paraformaldehyde in phosphate buffer and use of the inactivated cells to determine if haemophiliac patients have been inadvertently exposed to AIDS virus through blood transfusion. The data using sera samples from 50 haemophiliacs show that there is an increasing risk for these patients to contract AIDS, because of their need for blood transfusions to sustain life. L.W. Kitchen et al., *Nature,* 312, pp. 367 (Nov. 1984). This means that there is an urgent need for a safe, reliable and sensitive test to screen each blood sample before its inclusion in blood banks to isolate blood samples which have been contaminated with AIDS virus, and thus avoid the inadvertent spread of AIDS among patients who must receive blood transfusions, e.g. haemophiliac and surgical patients.

In November 1984 and January 1985, R. C. Gallo's group at National Cancer Institute and other collaborators positively concluded that HTLV-III is the causative agent of AIDS and reported the nucleotide sequence of HTLV-III. See Beatrice Hahn et al., *Nature,* 312, pp. 166 (Nov. 1984), George M. Shaw et al., *Science,* 226,pp. 1165 (Dec. 1984) and Lee Ratner et al., *Nature,* 313, pp. 277 (Jan. 1985).

Meanwhile, three other groups also reported the complete nucleotide sequence of the AIDS virus. See Muesing et al., *Nature,* 313, pp. 450 (Feb. 1985); Sanchez-Pescados, R. et al., *Science,* 227, pp. 484 (Feb. 1985) and Wain-Hobson et al., *Cell,* 40, pp. 9 (Jan. 1985). These reports elucidated the structure of the HTLV-III virus at both the DNA level and the projected protein level and permit further serological studies of the different epitopes present on the HTLV-III virus.

Simultaneously, the group at Institute Pasteur reported that LAV has been identified as a causative agent for AIDS, and is considered to be identical to HTLV-III. The assay procedure used by this group also involves propagating LAV in T4+ cells of healthy individuals. The viral antigen was then concentrated and deactivated in 0.5 per cent sodium dodecyl sulfate at 37° C. for 15 minutes. Serum samples were then tested against the antigen in an enzyme immunoassay with orthophenylene diamine as substrate. The presence of antibody in serum was found in 68% of AIDS patients, 100% of patients with Kaposi's sarcoma and 100% of pre-AIDS patients. Jeffrey Laurence et al., op. cit.

Recently, U.S. Pat. No. 4,520,113 was issued to R. C. Gallo et al.. The Gallo et al. patent describes a method of detecting antibodies in sera of AIDS and pre-AIDS patients by using lysates of a cell line, designated H9/HTLV-III, as the antigen in an enzyme-linked immunosorbent assay (ELISA) or in a strip radioimmunoassay based on the Western Blot technique or an indirect immunofluorescent method. The method is about 85% accurate. The Gallo patent further indicated that several antigens from HTLV-III, p65, (MW 65,000), p60 (MW 60,000), p55 (MW 55,000), p24 (MW 24,000) and p41 (MW 41,000) are recognized by antibodies in sera from AIDS patients, homosexuals and heroin addicts. Of these, major immune reactivity or specificity is directed against p41, a protein constituting the envelope antigen of HTLV-III. This patent further states that it is believed that additional purification and refinement of p41 may lead to an even more sensitive ELISA assay. Based on this statement, the antigen suitable as a test reagent is found to be a p41 segment derived from HTLV-III cultivated in H9 cell line.

It is further reported in Robert C. Gallo et al., *Science,* 228, pp. 93 (April 1985) that a combined cloning and expression system in *E. Coli* has been used to identify HTLV-III encoded peptides which react immunologically with antibodies in sera from AIDS patients. Cloned HTLV-III DNA was sheared into fragments and inserted into an expression vector. The inserted DNA was then expressed in *E. Coli* transformants. Of 300 clones tested, 20 showed specific reactivity with sera from AIDS patients. The 20 clones were analyzed and found to contain segments from the ORF segment of HTLV-III and were identified as clones 175, 191, 13, 31, 162, 113, 121 and 127. Of the eight clones, ORF clones 113, 121 and 127 define the protein encoded by the portion of the env-lor region produced by HTLV-III infected cells and induces antibody production in most if not all AIDS patients.

T.W. Chang et al, *Biotechnology,* 3, pp. 905 (October 1985) reported the use of a recombinant *E. Coli* derived viral antigenic peptide as being useful in an immuno assay for the detection of antibodies to HTLV III. The antigenic peptide is described as peptide 121 having a molecular weight of 15,000 daltons.

C. D. Cabradilla et al., *Biotechnology,* 4, pp. 125 (February 1986) also describes the use of a bacterially synthesized env polypeptide, having 102 amino acides for the serodiagnosis of antibodies to HTLV-III.

Cosand, U.S. Pat. No. 4,629,783 issued Dec. 16, 1986, described the use of chemically synthesized peptides conjugated to carriers as having immunoreactivity with antibodies to HTLV-III and useful as reagents in the determination of exposure of a human host to the virus. Seven peptides were described, of which two have sequences which are similar to the peptides herein described. One is a peptide having 13 amino acids, conjugated by acetylation to a carrier protein and having the following amino acids sequence:

Y-Arg-Ile-Leu-Ala-Val-Glu-Arg-Tyr-Leu-Lys-Asp-
Gln-Gln-Z-X wherein X is OH or $NH_2$, Y is an amino acid to facilitate coupling of the peptide to a carrier, N-terminally acetylated and linked to a peptide or protein of at least 5,000 molecular weight which peptide or protein does not normally bind to antibodies present in a human host. The other is a peptide having 26 amino acids acetylated and conjugated to a carrier protein having the following amino acids sequence:

-Arg-Ile-Leu-Ala-Val-Glu-Arg-Tyr-Leu-Lys-Asp-
Gln-Gln-Leu--Leu-Gly-Ile-Trp-Gly-Cys-Ser-Gly-
Lys-Leu-Ile-Cys-X wherein X is OH or $NH_2$, N-terminally acetylated and linked to a peptide or protein of at least 5,000 molecular weight which peptide or protein does not normally bind to antibodies present in a human host. Cosand also described that a mixture of polypeptide having an amino acids sequence corresponding to:

Y-Asp-Cys-Lep-Thr-Ile-Ley-Lys-Ala-Leu-Gly-
Pro-Ala-Ala-Thr-Leu-Glu-Glu-Met-Met-Thr-
Ala-Cys-X wherein Y and X has the same meaning defined above and a conjugated polypeptide having 26 amino acids, identified above, as having immunoreactivity that is stronger than the conjugated polypeptide having 26 amino acids alone.

Most of the reported assay procedures for detecting antibodies to HTLV-III and for diagnosis of AIDS or pre-AIDS conditions involve the use of the HTLV-III or LAV virus. The other assay procedures have not been tested sufficiently up to the present. None of the procedures are 100% accurate. This is undesirable for use in the screening of sera in blood banks. The less than 100% accuracy of the tests may permit contaminated sera from escaping detection and be used in blood transfusions to the severe detriment of blood recipients. Moreover, the use of the HTLV-III virus as the testing agent is dangerous to healthy laboratory workers, requiring extreme precautions to avoid all chances of exposure during the preparative process to make the test reagent. Furthermore, even though the deactivated virus is used in some of the published procedures, exposure to the deactivated virus can cause antibody production in healthy workers, who may then be falsely diagnosed as having AIDS, ARC or pre-AIDS condition. Moreover, presence of cellular materials from H9 cells or *E. Coli* in the test agent may elicit a false positive response in the HTLV-III antibodies screening test from individuals who have antibodies to *E. Coli* or H9 cells. These false positive reactions can bring severe anxiety to the healthy individuals and their family and may lead to a healthy individual being mistakenly diagnosed as having AIDS and be exiled from normal social activities as a consequence.

The number of tests reported in Cosand U.S. Pat. No. 4,629,783 is very small. The results indicate that the conjugated polypeptide with 26 amino acids is not as good as the deactivated virus. Moreover, Cosand does not describe the peptide composition of the present invention.

Furthermore, up to the present, no viable vaccine or method to provide protection against HTLV-III has been reported for AIDS, ARC or pre-AIDS conditions. The use of deactivated virus provokes fears of contracting the disease and would prevent its acceptability and use.

Similarly, the development of monoclonal and polyclonal antibodies to HTLV-III in mammals involves the use of HTLV-III as the immunogen and this presents similar risks in the procedure.

In Application Ser. Nos. 774,644, 837,566 and 847,102, applicants described a 21mer peptide with twenty-one (21) amino acids as a highly sensitive reagent for the detection of antibodies to HTLV-III, as a vaccine for protection against the AIDS virus, and for the production of monoclonal and polyclonal antibodies to AIDS virus. The contents of these applications are incorporated herein by reference.

Upon extensive clinical testing with the 21mer peptide at various blood banks and research institutes, it has been found that a small number, 12 out of 449, or about 2.67% of serum samples, mostly at the later stage of AIDS, which tested positive by Western Blot Analysis, gave negative results when tested against the 21mer peptide. Even though the percentage is small, this is considered to be disadvantageous, in that sera of possibly infected individuals may escape detection and be used for transfusion and in surgical procedures.

It is, therefore, an objective of the present invention to further perfect a detection or diagnostic procedure that will ensure detection of antibodies to HTLV-III in all individuals who may have been exposed to or was infected with HTLV-III.

A further objective is to develop a test procedure that is highly sensitive and 100% accurate, i.e. it will not produce false positive or false negative results.

BRIEF DESCRIPTION OF THE INVENTION

According to the present invention, a peptide composition comprising a peptide of thirty-five amino acids, a mixture of two peptides and optionally a third peptide as the immunogenic reagent for the detection of antibodies to HTLV-III. The peptide composition comprises a peptide of thirty-five amino acids, a mixture of a peptide of about twenty-one amino acids, a peptide of about nineteen amino acids and optionally a third peptide of about eleven amino acids. The peptides were made by solid phase peptide synthesis. The peptide composition has been found to be useful in a highly sensitive and accurate method for the detection of antibodies to HTLV-III in sera and body fluids and diagnosis of AIDS, ARC or pre-AIDS conditions. The peptide composition is useful in stimulating production of antibodies to HTLV-III or LAV in healthy mammals such as Balb/c mice.

According to the present invention, a peptide composition useful for the detection of antibodies to HTLV-III and diagnosis of AIDS, ARC or pre-AIDS conditions in sera or body fluids comprising:

A. a peptide having the following amino acids sequence Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-Thr-Thr-Ala-Val-Pro-Trp-Asn-Al a-Ser, analogues thereof and segments thereof; or B. a mixture of:

(i) about 10 to 95 parts by weight of Arg-Ile-Leu-Ala-Val-Glu-Arg-Tyr-Leu-Lys-Asp-Gln-Gln-Leu-Leu-Gly-Ile-Trp-Gly-Cys-Ser, analogues thereof and segment thereof;

(ii) about 5 to 90 parts by weight of Ile-Trp-Gly-Cys-Ser-Gly-Lys-Leu-Ile-Cys-Thr-Thr-Ala-Val-Pro-Trp-Asn-Ala-Ser, analogues thereof and segments thereof; and optionally (iii) about 5 to 50 parts by weight of Ile-Val-Arg-Met-Tyr-Ser-Pro-Thr-Ser-Ile-Leu, analogues thereof and segments thereof.

It is to be understood that the three letter codes used correspond to the named amino acids:

Ala=alanine,
Arg=arginine,
Asn=asparagine,
Asp=aspartic acid,
Gln=glutamine,
Glu=glutamic acid,
Gly=glycine,
Leu=leucine,
Lys=lysine,
Ile=isoleucine,
Pro=proline,
Met=methionine,
Ser=serine,
Thr=threonine,
Trp=tryptophan,
Tyr=tyrosine,
Val=valine, and
Cys=cysteine.

A highly sensitive and accurate method of detecting antibodies to HTLV-III in body fluids and diagnosis of AIDS, ARC or pre-AIDS condition comprises the following steps:

A. Preparing a peptide composition selected from the group comprising:

a. a peptide having the following amino acids sequence Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-Thr-Thr-Ala-Val-Pro-Trp-Asn-As n-Ala-Ser, analogues thereof and segments thereof; or b. a mixture of:

(i) about 10 to 95 parts by weight of Arg-Ile-Leu-Ala-Val-Glu-Arg-Tyr-Leu-Lys-Asp-Gln-Gln-Leu-Leu-Gly-Ile-Trp-Gly-Cys-Ser, analogues thereof and segments thereof;

(ii) about 5 to 90 parts by weight of Ile-Trp-Gly-Cys-Ser-Gly-Lys-Leu-Ile-Cys-Thr-Thr-Ala-Val-Pro-Trp-Asn-Ala-Ser, analogues thereof and segments thereof; and optionally (iii) about 5 to 50 parts by weight of Ile-Val Arg-Met-Tyr-Ser-Pro-Thr-Ser-Ile-Leu, analogues thereof and segments thereof.

B. Using about 0.1 ug to about 20 ug per test of the peptide composition as the antigen in an immuno assay procedure.

Further, according to the present invention, the peptide when coupled to a protein or a polymer carrier, or in a polymerized form can be used to stimulate production of antibodies to HTLV-III or LAV in healthy mammals including humans. The method comprises introducing an effective amount of the peptide composition, wherein each peptide is conjugate to a protein, such as human serum albumin into the body of a healthy mammal by intraperitoneal or subcutaneous injection.

DETAILED DESCRIPTION OF THE INVENTION

In accordance with the present invention a peptide composition has been chemically synthesized and prepared for the detection of antibodies to HTLV-III in body fluids and diagnosis of AIDS, ARC and pre-AIDS condition, for the vaccination of healthy mammals by stimulating the production of antibodies to HTLV-III or LAV in healthy mammals, and for the development of both monoclonal and polyclonal antibodies to HTLV-III in mammals.

The peptide composition comprises:

A. a peptide having the following amino acids sequence: Arg-Ile-Leu-Ala-Val-Glu- Arg-Tyr-Leu-Lys-Asp-Gln-Gln-Leu-Leu-Gly-Ile-Trp-Gly-Cys-Ser-Gly-Lys-Leu-Ile-Cys-Thr-Thr-Ala-Val-Pro-Trp-Asn Ala-Ser, analogues thereof and segments thereof; or B. a mixture of two peptides:

(i) about 10 to 95 parts by weight of a peptide of about twenty one amino acids, analogues or segments thereof arranged in the following sequence: Arg-Ile-Leu-Ala-Val-Glu-Arg-Tyr-Leu-Lys-Asp-Gln-Gln-Leu-Leu-Gly-Ile-Trp-Gly-Cys-Ser (ii) about 5 to 90 parts by weight of a peptide of about nineteen amino acids, analogues or segments thereof arranged in the following sequence: Ile-Trp-Gly-Cys-Ser-Gly-Lys-Leu-Ile-Cys-Thr-Thr-Ala-Val-Pro-Trp-Asn-Ala-Ser.

The mixture may further include 5 to 50 parts by weight of a peptide of about eleven amino acids, analogues or segments thereof arranged in the following sequence: Ile-Val-Arg-Met-Tyr-Ser-Pro-Thr-Ser-Ile-Leu.

Each of the peptides may comprise a shorter or longer peptide chain by having more amino acids added to the terminal amino acids of the above sequences or having a few less of the terminal amino acids from either terminal of each of the peptides.

It is expected that as long as the three dimensional conformations of each of the three peptides recognizable by the dominant antibodies to HTLV-III are preserved, the synthetic peptide composition may comprise analogues of the recited amino acids of the above sequences. The term "analogues" encompasses each of the entire peptides, portions thereof, peptides that contain substitutions of amino acid residues, insertions and/or deletions of amino acids, or polymeric forms of the peptides. These analogues can also be used to detect and/or elicit production of antibodies to HTLV-III.

The amino acid sequences of the 35mer, 21mer and 19mer peptides in the peptide composition useful as a test reagent for the detection of antibodies to HTLV-III in body fluids and diagnosis of AIDS, ARC and pre-AIDS condition is prepared to correspond to a partial segment of the amino acid sequence of the HTLV-III virus designated as p41, a part of p160, the LOR (long open reading) segment, defining the envelope protein of the HTLV-III virus. The amino acid sequence of the 11mer peptide is prePared to correspond to a partial segment of the amino acid sequence of the HTLV-III virus core protein designated as p24, the gag segment.

The peptides useful as the solid phase immunoadsorbent for the detection of antibodies HTLV-III were synthesized by "classical" Merrifield method of solid phase peptide synthesis according to the following scheme.

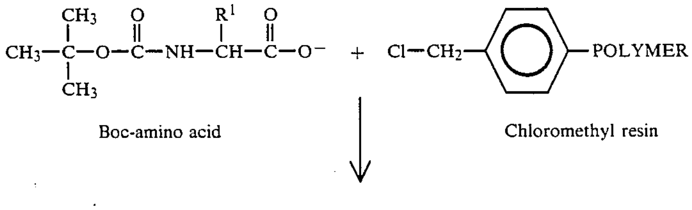

Boc-amino acid

Chloromethyl resin

-continued

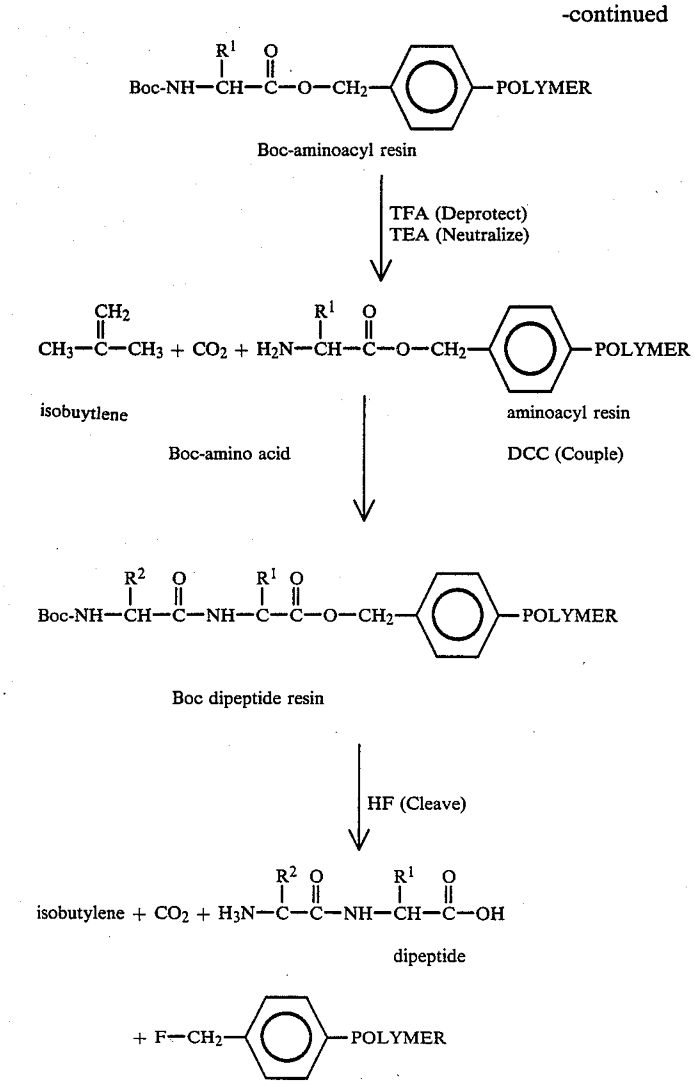

Following the above scheme, Boc-amino acids are added to the resin to prepare the 35mer peptide, the 21mer peptide, the 19mer peptide and the 11mer peptide.

Analogues of each of the peptides can be prepared by varying the above sequence either by adding or subtracting desired Boc-amino acid(s).

Following completion of assembly of the desired blocked peptide on the resin, the peptide-resin is treated with anhydrous hydrofluoric acid to cleave the benzyl ester linking the peptide to the resin in order to liberate the peptide. Side-chain functional groups of amino acids which are blocked during synthesis by benzyl-derived blocking groups are also cleaved from the peptide simultaneously. The free peptide is then analyzed and purified by reverse phase high pressure liquid chromotography (HPLC) and characterized biochemically by amino acid analysis.

Similarly, synthesis of each of the peptides that has an amide group on its C-terminal end can be achieved by using a 4-methylbenzhydrylamine resin according to the following scheme:

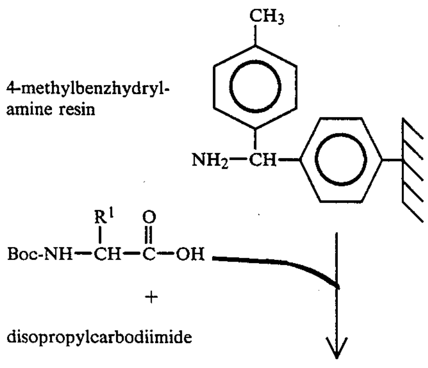

-continued

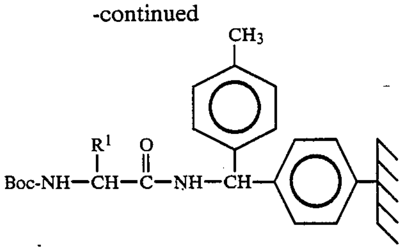

Coupling the C-terminal Residue to 4-Methybenzhydryl amine residue

The peptide composition synthesized according to the above described procedure is highly reactive to antibodies to HTLV-III and can be used as a highly sensitive, accurate, reliable and specific immunoadsorbent for the detection of antibodies against HTLV-III. Results obtained with the peptide composition according to the present invention show that it is more sensitive and specific to antibodies against HTLV-III in body fluids than the Western Blot method, the standard method used for the diagnosis of AIDS. See Tables I, II and III.

It can be observed from Table III that the 35mer peptide has the highest immunoreactivity. However, it is preferable to use a mixture of the 21mer and 19mer peptides, which have amino acids sequences overlapping the 35mer peptide, because it is much more difficult and costly to synthesize the longer chain peptide. This is because the yield of the synthesis process becomes increasingly low for peptides with increasing length.

Based on the high degree of sensitivity and specificity of the peptide composition according to the present invention in the immunoreaction to antibodies to HTLV-III, it is believed that it is also useful as a vaccine for AIDS, ARC or pre-AIDS conditions, and as an immunogen for the development of both monoclonal and polyclonal antibodies to HTLV-III in mammals. The peptide composition as the 35mer peptide or a mixture of each of the peptide itself or when coupled to a protein or a polymer carrier, can be introduced to normal subjects to stimulate production of antibodies to HTLV-III, and provide protection against infection by HTLV-III or LAV in healthy individuals. Since the peptide composition according to the present invention is not derived biochemically from the virus, there is no danger of exposing the normal subjects who are to be vaccinated to the disease.

It has been found that when the 21mer peptide conjugated to human serum albumin (HSA), as the carrier protein, was injected intraperitoneally and subcutaneously into healthy Balb/c mice, antibodies to the 21mer peptide cross reactive with HTLV-III were produced by the Balb/c mice. See Application Ser. No. 847,102 and Table IV.

The results obtained indicate that the 21mer peptide is also useful as an immunogen for the development of both monoclonal and polyclonal antibodies to HTLV-III in mammals.

Based on the results obtained with the 21mer peptide, it is expected that the peptide composition will also stimulate the production of antibodies to HTLV-III and provide protection against infection by HTLV-III or LAV in healthy individuals. It is also expected that the peptide composition will also be useful as an immunogen for the development of both monoclonal and polyclonal antibodies to HTLV-III in mammals. See Application Ser. No. 847,102, Examples 7 and Table IV.

The advantages of using the peptide composition according to the present invention are many.

The peptide composition is chemically synthesized. This means that there is no involvement with the HTLV-III virus at any time during the process of making the test reagent or the vaccine. During the preparation of the vaccine or the vaccination process, there is no risk of exposure of the production workers, individuals in the health profession and those being vaccinated to the HTLV-III virus. Similarly, there is no risk of exposure to HTLV-III in the use of the peptide composition for the development of monoclonal or polyclonal antibodies to HTLV-III in mammals. Further, up to the final step of the test to detect antibodies to HTLV-III, where the test reagent is exposed to the samples of sera or body fluid, there is no risk of exposure of the laboratory worker to the HTLV-III virus. And, risk of exposure in this final step can be avoided by taking the precautionary step of deactivating any virus which may be present by heating at 60° C for half an hour the samples of sera or body fluids which are to be tested.

Another problem which is avoided by the process of the present invention is the possibility of false positive results caused by the presence of antigenic material from H9 cells co-purified with the HTLV-III viral preparation or *E-Coli* derived proteins co-purified with expressed viral fragments. Certain normal individuals have antibodies to E. Coli or human leukocyte antigens, e.g. HLA, which are cross reactive with the antigenic materials from H9 cells. Sera samples from these normal individuals may show a positive response in the ELISA or IRMA test even though they have not been exposed to HTLV-III. A diagnosis that a person may be inflicted with AIDS based on this type of false positive response can bring severe anxiety to the person and his/her family, and cause him/her to be excluded from normal social activities. All of these problems can be avoided by using the peptide of the present invention as the test reagent.

A third problem which has plagued this area is the possibility of false negative results. The accuracy of the results using the 21mer peptide alone is about 98% whereas the accuracy of the results using the peptide composition as the antigen is 100% using the following as the cutoff point:

$$\text{Cutoff point} = 0.1 \times A_{492}(RC) + 1 \times \times A_{492}(NRC)$$

where $A_{492}(RC)$ is the absorbance reading for the reactive control and $A_{492}(NRC)$ is the absorbance reading for the non-reactive control.

In fact, the ELISA method using the peptide composition of the present invention in certain cases gave a positive indication confirmed by medical diagnosis where the standard Western Blot test produced a negative result. This indicates that the present method is even more accurate than the Western Blot test.

Extensive clinical trials were conducted on 140 seroconverted specimens collected during the period of late 1979 to 1982 from healthy homosexuals in New York City originally selected for Hepatitis B vaccine studies. These serum samples were also characterized by Western Blot analysis and HTLV-III ELISA tests of the present invention. The results of the tests showed that the sensitivity of the ELISA method using the peptide composition of the present invention is much higher than that of the Western Blot Analysis. Moreover, using the ELISA method with the peptide composition produced Ppsitive signals in eleven individuals well before the p24, p55 and P17 bands appeared in the Western Blot Analysis. Similarly, the ELISA method with the peptide composition of the invention is more sensitive and produced earlier diagnostic results than that of ELISA test kits presently available in the market.

Further, with appropriate amino acid analogue substitutions, it is expected that various peptide analogues based on the prescribed amino acid sequences can be synthesized with properties giving rise to lower background readings or better adsorption capacity to solid phases useful for HTLV-III antibodies screening assays.

Various peptide analogs based on the above described amino acid sequence have been prepared. These analogs and their reactivities with the anti HTLV-III antibodies present in sera of AIDS and ARC patients are described in Example 8 and Table III. The reactivity in an ELISA test for the same amount of each peptide by weight per volume was compared with the reactivity of the 21mer peptide, which was assigned a reactivity of 100.

Our results indicate at the 21mer peptide of the present invention is unique in its size and sequence in that mere deletion of -Arg-, or -Ile- from the N- terminal or -Trp-Gly-Cys-Ser- from the C-terminal, or cleaving this peptide in between the -Lys- and -Asp- to form two peptides of 10 and 11 amino acids, all resulted in dramatic loss of antigenicity conferred by the 21mer peptide. In addition, -Lys- at position 12 from the C-terminal also appears to be important, in that addition of -Lys- to the above said peptide with 11 amino acids restores significantly the antigenicity. Similarly C-terminal amino acids such as -Ile-Trp-Gly-Cys-Ser- also play an important role in the antigenicity to the antibody-antigen interaction. See Table III, peptides 4 and 6.

Analogues of the 19mer peptide have also been prepared to produce similar results. See Table III. The 19mer peptide also shares at its N-terminal the amino acid sequences of Ile-Trp-Gly-Cys-Ser with the 21 mer peptide. This again clearly demonstrates the importance of this region. Deletion of the segment from the 19mer resulted in the complete loss of antigenicity.

The 11mer peptide has an amino acid sequence corresponding to a segment of the gag protein. A comparison of ELISA results using the 11mer peptides as the solid phase immuno adsorbent with Western Blot shows that the 11mer peptide is highly immunoreactive. Using a total of 266 samples of which 159 had been shown to be p24 positive and 107 were shown be p24 negative by the Western Blot method, the 11mer peptide showed corresponding results for 114 out of the 159 and 105 out of the 107. See Example 10 and Table V.

Moreover, because the peptides of the present invention are synthetically prepared, the quality can be controlled, and as a result, reproducibility of the test results can be assured. Also, since very small amounts of the peptides are required for each test procedure, and the expense of preparing the peptide is relatively low, the cost of screening body fluids for antibodies to HTLV-III and diagnosis of AIDS, ARC or pre-AIDS and the preparation of a vaccine is relatively low.

The peptide composition prepared in accordance with the present invention can be used to detect HTLV-III infection and diagnose AIDS, ARC and pre-AIDS condition by using it as the test reagent in an enzyme-linked immunosorbent assay (ELISA), an enzyme immunodot assay, a hemagglutination assay or a radioimmunoradiometric assay (IRMA), preferably ELISA. The ELISA technique using a mixture of the 21mer and 19mer peptides is exemplified in Example 1, the ELISA method with a mixture of the 21mer peptide, 19mer peptide and 11mer peptide is exemplified in Example 2.

It is to be noted that in the following methods, 0.25% by weight of glutaldehyde may be added in the coating buffer to facilitate better peptide binding onto the plates or beads. Further, horseradish peroxidase conjugated mouse monoclonal anti human IgG antibody may be used in place of horseradish peroxidase conjugated goat anti human IgG as a second antibody tracer. The gelatins useful in these processes can include calf skin gelatin, pig skin gelatin, fish gelatin or any known available gelatin proteins or be replaced with albumin proteins.

The following examples illustrates the invention and are to be construed as limiting the scope thereof.

EXAMPLE 1

Detection of Antibodies to HTLV-III by an Enzyme-Linked Immunoadsorbent Assay A mixture in a ratio by weight of 10:1 of the 21mer and 19mer peptides, synthesized as described was prepared.

Wells of 96-well plates were coated at 37° C for 1 hour with the mixture of the 21mer peptide and the 19mer peptide, at 1.0 ug per well in 100 ul 0.1 M $NaHCO_3$ buffer, pH 9.5. The wells were washed three times with phosphate buffered saline (PBS) and then incubated with 250 ul of 3% by weight gelatin in PBS at 37° C. for 1 hour to block non-specific protein binding sites, followed by three more washes with PBS containing 0.05% by volume Tween 20. The test sera (blood taken from a human patient or normal individual) were diluted with PBS containing 20% by volume normal goat serum, 1% by weight gelatin and 0.05% by volume Tween 20 at a dilution of 1:20, volume to volume, respectively. 200 ul of the diluted sera were added to each well and allowed to react for 15 minutes at 37° C. The wells were then washed six times with 0.05% by volume Tween 20 in PBS in order to remove unbound antibodies. Horseradish peroxidase conjugated goat anti human IgG was used as a second antibody tracer to bind with the AIDS antibody-antigen complex formed in positive wells. 100 ul of peroxidase labeled goat anti human IgG at a dilution of 1:3000 in 1% by volume normal goat serum, 0.05% by volume Tween 20 in PBS was added to each well and incubated at 37° C for another 15 minutes.

The wells were washed six times with 0.05% by volume Tween 20 in PBS to remove unbound antibody and reacted with 100 ul of the substrate mixture containing 0.04% by weight orthophenylenediamine (OPD) and 0.012% by volume hydrogen peroxide in sodium citrate buffer, pH 5.0. The mixture was incubated at 37° for 15 min. This substrate mixture was used to detect the peroxidase label by forming a color product. Reactions were stopped by the addition of 100 ul of 2.N $H_2SO_4$ and the color yield measured using an ELISA reader which quantifies the color reading at 492nm (i.e. OD was measured at 492nm). Assays were performed with 1:20 dilution. Normal serum samples were used as nonreactive controls. Sera samples obtained from an individual diagnosed as having AIDS is included as reactive controls. Absorbence readings greater than a cut off absorbance reading determined according to the following formula were taken as positive.

$$\text{Cutoff point} = 0.1 \times A_{492}(RC) + 1 \times A_{492}(NRC)$$

wherein $A_{492}(RC)$ is the absorbance reading for the reactive control and $A_{492}(NRC)$ is the absorbance reading for the non-reactive control. The results are shown in Table I.

TABLE I

Comparison of ELISA using a 10:1 mixture of 21mer and 19mer peptides with Western Blot Analysis

| Patient Diagnosis | No. Positive/No. Tested ELISA | Western Blot |
|---|---|---|
| Acquired Immunodeficiency Syndrome | 187/187 | 186/187 |
| Pediatric AIDS | 11/11 | 11/11 |
| AIDS related complex | 116/116 | 116/116 |
| Persistent Generalized Lymphoadnopathy | 29/29 | 29/29 |
| Lymphadenophathy | 6/7 | 6/7 |
| Healthy Homosexuals | 48/57 | 48/57 |
| Transexual | 1/1 | 1/1 |
| Bisexual | 0/3 | 0/3 |
| Intravenous Drug Abuser | 20/21 | 20/21 |
| Sexual Partner of AIDS patient | 12/18 | 12/18 |
| Hemophiliac | 6/6 | 6/6 |
| Transfusion | 3/3 | 3/3 |
| Idiopathic Thrombocytopenic Purpura | 1/1 | 1/1 |
| Non-AIDS KaPosi's Sarcoma | 0/3 | 0/3 |
| Health Care Worker (mostly with needle sticks) | 0/14 | 0/14 |
| Acute Myelogenous Leukemia | 0/12 | 0/12 |
| Chronic Myelogenous Leukemia | 0/2 | 0/2 |
| Acute Lymphocytic Leukemia | 0/6 | 0/6 |
| Chronic Lymphocytic Leukemia of the B type | 0/32 | 0/32 |
| Chronic Lymphocytic Leukemia of the T type | 0/2 | 0/2 |
| Non-Hodgkin's Lymphoma | 0/4 | 0/4 |
| Hodgkin's Disease | 0/1 | 0/1 |
| Hairy Cell Leukemia | 1/2 | 1/2 |
| Macroglobulinemia | 0/1 | 0/1 |
| Mycosis Fungoide | 0/1 | 0/1 |
| Primary Immunodeficiency including Common variable immunodeficiencies, Hypogammaglobulinemia and Thymoma | 0/25 | 0/25 |
| Gamma Globulin Preparation | 0/1 | 0/1 |
| Other Diseases Unrelated to HTLV-III infection | | |
| Viral infections | 1/6 | 1/6 |
| Sarcoidosis | 0/2 | 0/2 |
| Patient with papilloma | 0/1 | 0/1 |
| Non-AIDS | 0/3 | 0/3 |
| Normal Control | 0/38 | 0/38 |
| Brother of AIDS patient | 0/1 | 0/1 |
| Daughter of AIDS patient | 0/1 | 0/1 |
| Wife of AIDS patient | 1/2 | 1/2 |
| Infant of AIDS patient | 0/1 | 0/1 |
| Repeat reactive by Abbott test | 7/54 | 7/54 |
| | 450/674 | 449/674 |

The results in Table I of the ELISA test procedure according to the present invention with 674 sera samples show that the method is extremely accurate and highly specific. No immunoreactivity was found in normal subjects or patients who were identified as not being inflicted with AIDS or ARC. In fact, the ELISA results confirmed medical diagnosis of AIDS which was missed by Western Blot Analysis.

It is to be noted that the cut off absorbance reading is very stringent. It was determined statistically based upon a large number of clinical trial data (larger than 10,000 tests).

EXAMPLE 2

The procedure of Example 1 was repeated using the same sera samples as in Example 1 except that the well plates were precoated with a mixture of the 21mer peptide, 19mer peptide and 11mer peptide in a weight ratio of 10:1:1. The results are presented in Table II.

TABLE II

Comparison of ELISA using a 10:1:1 mixture of 21mer, 19mer and 11mer peptides with Western Blot Analysis

| Patient Diagnosis | No. Positive/No. Test ELISA | Western Blot |
|---|---|---|
| Acquired Immunodeficiency Syndrome (AIDS/KS, AIDS/IVDA, AIDS/HD, AIDS/OI etc.) | 187/187 | 186/187 |
| Pediatric AIDS | 11/11 | 11/11 |
| AIDS related complex | 116/116 | 116/116 |
| Persistent Generalized Lymphoadnopathy | 29/29 | 29/29 |
| Lymphadenophathy | 6/7 | 6/7 |

TABLE II-continued

Comparison of ELISA using a 10:1:1 mixture of 21mer, 19mer and 11mer peptides with Western Blot Analysis

| Patient Diagnosis | No. Positive/No. Test ELISA | Western Blot |
|---|---|---|
| Healthy Homosexuals | 48/57 | 48/57 |
| Transexual | 1/1 | 1/1 |
| Bisexual | 0/3 | 0/3 |
| Intravenous Drug Abuser | 20/21 | 20/21 |
| Sexual Partner of AIDS patient | 12/18 | 12/18 |
| Hemophiliac | 6/6 | 6/6 |
| Transfusion | 3/3 | 3/3 |
| Idiopathic Thrombocytopenic Purpura | 1/1 | 1/1 |
| Non-AIDS Kaposi's Sarcoma | 0/3 | 0/3 |
| Health Care Worker(mostly with needle sticks) | 0/14 | 0/14 |
| Acute Myelogenous Leukemia | 0/12 | 0/12 |
| Chronic Myelogenous Leukemia | 0/2 | 0/2 |
| Acute Lymphocytic Leukemia | 0/6 | 0/6 |
| Chronic Lymphocytic Leukemia of the B type | 0/32 | 0/32 |
| Chronic Lymphocytic Leukemia of the T type | 0/2 | 0/2 |
| Non-Hodgkin's Lymphoma | 0/4 | 0/4 |
| Hodgkin's Disease | 0/1 | 0/1 |
| Hairy Cell Leukemia | 1/2 | 1/2 |
| Macroglobulinemia | 0/1 | 0/1 |
| Mycosis Fungoide | 0/1 | 0/1 |
| Primary Immunodeficiency including Common variable immunodeficiencies, Hypogammaglobulinemia and Thymoma | 0/25 | 0/25 |
| Gamma Globulin Preparation | 0/1 | 0/1 |
| Other Diseases Unrelated to HTLV-III infection | | |
| Viral infections | 1/6 | 1/6 |
| Sarcoidosis | 0/2 | 0/2 |
| Patient with papilloma | 0/1 | 0/1 |
| Non-AIDS | 0/3 | 0/3 |
| Normal Control | 0/38 | 0/38 |
| Brother of AIDS patient | 0/1 | 0/1 |
| Daughter of AIDS patient | 0/1 | 0/1 |
| Wife of AIDS patient | 1/2 | 1/2 |
| Infant of AIDS patient | 0/1 | 0/1 |
| Repeat reactive by Abbott test | 7/54 | 7/54 |
| | 450/674 | 449/674 |

The above results indicate that the 11mer peptide may also be included in the immuno assay procedure to produce similar results as shown for the mixture of 21mer and 19mer peptides.

EXAMPLE 3

Detection of Antibodies to HTLV-III by an Immunoradiometric Assay (IRMA)

Wells of 96-well flexible-polyvinylchloride (PVC) plates are coated at 37° C. for 1 hour with a mixture of 10:1:1 by weight of the 21mer peptide, the 19mer peptide and 11mer peptide, prepared as described, at 1.0 ug per well in 100 ul 0.1M $NaHCO_3$ buffer, pH 9.5. The wells are washed three times with phosphate buffered saline (PBS) and then incubated with 250 ul of 3% by weight gelatin in PBS at 37° C for 1 hour to block non-specific protein binding sites, followed by three more washes with PBS containing 0.05% by volume Tween 20. The test sera (blood taken from a human patient or normal individual) are diluted with PBS containing 20% by volume normal goat serum, 1% by weight gelatin and 0.05% by volume Tween 20 at a dilution of 1:20 (volume to volume) respectively 200 ul of the diluted sera are added to each well and allowed to react for 15 minutes at 37° C. The wells are then washed six times with 0.05% by volume Tween 20 in PBS in order to remove unbound antibodies. $I^{125}$ labeled affinity purified goat anti human IgG (Fc) is used as a second antibody tracer that binds with the antibody-antigen complex formed in positive wells. 100 ul of $I^{125}$ labeled goat anti human IgG of 50,000–200,000 cpm in 1% by volume normal goat serum, 0.05% by volume Tween 20 in PBS was added to each well and incubated at 37° C. for 15 minutes.

The wells were washed five times with 0.05% by volume Tween 20 in PBS to remove unbound second antibody and dried. The wells are cut and counted by a gamma-scintillation counter Assays are performed in with 1:20 dilution, volume to volume, respectively. Normal sera samPle as negative controls were also tested simultaneously. Cpm readings greater than the average readings of normal sera samples +4 SD (standard deviation) are taken as positive.

EXAMPLE 4

Detection of Antibodies to HTLV-III by a Hemagglutination Assay using 10:1 Mixture of the Peptide Composition Coated Gelatin Particles, Sheep Red Blood Cells or Latex Beads as Solid Phase Immunoadsorbent One ml thoroughly washed human blood cells, Ox red blood cells, gelatin particles, or polystyrene latex beads are coated with a 10:1 by weight mixture of the 21mer peptide and the 19mer peptide at a concentration in the range of 1 ug/ml to 1 mg/ml. The coated cells, particles or beads are then incubated with serially diluted serum samples in the wells of a multi-well U-shaped or lattice shaped microplate. After being left at room temperature for about an hour, the agglutination patterns on the bottom are read, and the largest dilution showing a positive reaction is recorded.

This is a one-step assay which could be used for both qualitative and quantitative analysis of the presence of anti-HTLV-III antibodies in specimens including sera or biofluids.

EXAMPLE 5

A diagnostic AIDS, ARC and pre-AIDS specific test kit for HTLV-III antibodies detection can be constructed. The test kit comprises a compartmented enclosure containing multiple 96-well plates coated prior to use with 1 ug of the peptide composition of the present invention in 100 ul pH 9.5 0.1M $NaHCO_3$ buffer per well. The kit further comprises materials for enzyme detection in separate sealed containers consisting of: 1) normal human serum (as non reactive control); 2) heat inactivated, NP40 solubilized AIDS serum (as reactive control); 3) normal goat serum; 4) peroxidase labelled-goat anti human IgG; and 5) a color change indicator consisting of orthophenylenediamine (OPD) and hydrogen peroxide in phosphate citrate buffer. The procedure described in Example 1 is to be followed.

In this test kit, 96-well plates, precoated with the peptide of the present invention, can be replace by polystyrene beads, latex particles, or multiple mini-columns filled with controlled pore size glass beads, or nitrocellulose paper strip precoated with the peptide of the present invention for use as the solid phase immunoadsorbent.

EXAMPLE 6

A second test kit for detecting antibodies using the immunoradiometric assay (IRMA) comprises a compartmented enclosure containing multiple 96-well bendable polyvinylchloride (PVC) plates precoated with the peptide composition according to the present invention at a concentration of 1 ug of peptide composition in 100 ul of pH 9.5 0.1M $NaHCO_3$ buffer per well and materials for radioimmunoassay including: 1) normal human serum (as non-reactive control); 2) heat inactivated, NP40 solubilized AIDS serum (as reactive control); 3) normal goat serum; and, 4) $I^{125}$ labeled coated anti human IgG. The procedure described in Example 3 is to be followed.

In this test kit, 96-well PVC plates precoated with the peptide of the present invention can be replaced by polystyrene beads precoated with the peptide of the present invention for use as the solid phase immunoadsorbent.

EXAMPLE 7

A third test kit for detecting HTLV-III antibodies using the hemagglutination assay comprised a compartmented enclosure containing multiple 96-well U-shaped or latticed shaped microplates and materials for hemagglutination assay including (1) a bottle of human 0 red blood cells, Ox red blood cells, gelatin particles or latex polystyrene beads Precoated with a mixture of 10:1:1 by weight of the peptide composition (2) normal human serum (as a non-reactive control); and, (3) heat inactivated, NP40 solubilized AIDS positive serum (as reactive control). The procedure described in Example 4 is to be followed.

EXAMPLE 8

The 35mer peptide, 19mer peptide, 11mer peptide and eight analogues of the 21mer peptide, and overlapping 19mer peptide were prepared in their amide form according to the classical Merrifield method described herein above. The amino acid sequence of each of the analogues are shown in Table III.

The immunoreactivity of the various peptides at 1 ug per well level was tested using a pooled AIDS serum sample. The reactivity of each peptide was compared with the reactivity of the 21mer peptide which was set as 100%.

TABLE III

| Peptide | Amino Acid Sequence | Reactivity % |
|---|---|---|
| 1 | Val—Trp—Gly—Ile—Lys—Gln—Leu—Gln—Ala—Arg—Ile—Leu—Ala—Val—Glu—Arg—Tyr—Leu—Lys | 5 |
| 2 | Gln—Leu—Gln—Ala—Arg—Ile—Leu—Ala—Val—Glu—Arg—Tyr—Leu—Lys | 13.5 |
| 3 | Arg—Ile—Leu—Ala—Val—Glu—Arg—Tyr—Leu—Lys | 5 |
| 4 | Arg—Ile—Leu—Ala—Val—Glu—Arg—Tyr—Leu—Lys—Asp—Gln—Gln—Leu—Leu—Gly—Ile | 28.3 |
| 5 | Ile—Leu—Ala—Val—Glu—Arg—Tyr—Leu—Lys—Asp—Gln—Gln—Leu—Leu—Gly—Ile | 30.3 |
| 6 | Arg—Ile—Leu—Ala—Val—Glu—Arg—Tyr—Leu—Lys—Asp—Gln—Gln—Leu—Leu—Gly—Ile—Trp—Gly—Cys—Ser | 100 |
| 7 | Arg—Leu—Ala—Val—Glu—Arg—Tyr—Leu—Lys—Asp—Gln—Gln—Leu—Leu—Gly—Ile—Trp—Gly—Cys—Ser | 66.8 |
| 8 | Val—Glu—Arg—Tyr—Leu—Lys—Asp—Gln—Gln—Leu—Leu—Gly—Ile—Trp—Gly—Cys—Ser | 53.9 |
| 9 | Lys—Asp—Gln—Gln—Leu—Leu—Gly—Ile—Trp—Gly—Cys—Ser | 38.3 |
| 10 | Asp—Gln—Gln—Leu—Leu—Gly—Ile—Trp—Gly—Cys—Ser | 8 |
| 11 | Ile—Leu—Ala—Val—Glu—Arg—Tyr—Leu—Lys—Asp—Gln—Gln—Leu—Leu—Gly—Ile—Trp—Gly—Cys—Ser | 20.0 |
| 12 | Gly—Lys—Leu—Ile—Cys—Thr—Thr—Ala—Val—Pro—Trp—Asn—Ala—Ser | 2.42 |
| 13 | Cys—Ser—Gly—Lys—Leu—Ile—Cys—Thr—Thr—Ala—Val—Pro—Trp—Asn—Ala—Ser | 57.5 |
| 14 | Ile—Trp—Gly—Cys—Ser—Gly—Lys—Leu—Ile—Cys—Thr—Thr—Ala—Val—Pro—Trp—Asn—Ala—Ser | 99.0 |
| 15 | Leu—Lys—Asp—Gln—Gln—Leu—Leu—Gly—Ile—Trp—Gly—Cys—Ser—Gly—Lys—Leu—Ile—Cys—Thr—Thr—Ala—Val—Pro—Trp—Asn—Ala—Ser | 73.4 |
| 16 | Ala—Val—Glu—Arg—Tyr—Leu—Lys—Asp—Gln—Gln—Leu—Leu—Gly—Ile—Trp—Gly—Cys—Ser—Gly—Lys—Leu—Ile—Cys—Thr—Thr— Ala—Val—Pro—Trp—Asn—Ala—Ser | 107.1 |
| 17 | Arg—Ile—Leu—Ala—Val—Glu—Arg—Tyr—Lys—Leu—Asp—Gln—Gln—Leu—Leu—Gly—Ile—Trp—Gly—Cys—Ser—Gly—Lys—Leu—Ile—Cys—Thr—Thr— Ala—Val—Pro—Trp—Asn—Ala—Ser | 132.0 |

EXAMPLE 9

Varying Amounts of a mixture of 21mer Peptide and 19 mer Peptide

Following the procedure described in Example 1, mixtures of the 21mer peptide with the 19mer peptide with various weight ratios, from 10:1.25 to 4:1, were used as the immunoadsorbent. The wells were coated with 1 ug of the mixture. The serum samples used were two samples from patients which had been diagnosed as positive for AIDS and two samples from patients with autoimmune diseases. The two AIDS positive samples were screened out from over 500 HTLV III positive AIDS serum specimens and had been showned to be negative in ELISA using only the 21mer peptide as the immunoadsorbent. The results are shown in Table IV. The results indicate that the various mixtures of the 21mer and 19mer peptides gave more accurate results than the 21mer peptide alone.

TABLE IV

| Weight Ratio of Peptide Composition | | | Absorbance | | | | | |
|---|---|---|---|---|---|---|---|---|
| 21mer ug/ml | + | 19mer ug/ml | Positive Control | Normal Serum | AIDS Positive Samples 1 | AIDS Positive Samples 2 | Autoimmune Diseases 1 | Autoimmune Diseases 2 |
| 5 | | 0 | 1.01 | 0.03 | 0.04 | 0.05 | 0.09 | 0.04 |
| 5 | | 0.625 | 1.17 | 0.02 | 0.62 | 0.46 | 0.07 | 0.04 |
| 5 | | 1.25 | 1.30 | 0.02 | 1.16 | 1.08 | 0.07 | 0.03 |
| 5 | | 2.50 | 1.50 | 0.02 | 1.57 | 1.76 | 0.07 | 0.04 |
| 7.5 | | 0 | 0.92 | 0.03 | 0.04 | 0.06 | 0.09 | 0.05 |
| 7.5 | | 1.25 | 1.28 | 0.02 | 1.12 | 0.94 | 0.08 | 0.07 |
| 7.5 | | 2.5 | 1.54 | 0.03 | 1.58 | 1.59 | 0.07 | 0.04 |
| 10.0 | | 0 | 0.98 | 0.03 | 0.04 | 0.06 | 0.09 | 0.05 |
| 10.0 | | 0.625 | 1.11 | 0.02 | 0.51 | 0.33 | 0.09 | 0.07 |
| 10.0 | | 1.25 | 1.31 | 0.02 | 1.02 | 0.86 | 0.09 | 0.06 |
| 10.0 | | 2.50 | 1.72 | 0.03 | 1.69 | 1.67 | 0.09 | 0.07 |

EXAMPLE 10

1 ug of the 11mer peptide was used to coat each well of a 96-well plate. The procedure of Example 1 was followed. 266 serum samples were screened on the 11mer coated plate. The results are shown in Table V. Out of the 159 samples indicated as sero-positive by Western Blot Analysis, the 11mer peptide showed reactivity with 114 samples. Out of the 107 samples indicated as sero-negative by Western Blot Assay, the 11mer peptide showed non-reactivity with 105 samples.

The results indicates that the 11mer peptide is immunoreactive with antibodies to HTLV-III.

TABLE V

Comparison of ELISA using 11mer Peptide with Western Blot Method

| ELISA | | WESTERN BLOT | |
|---|---|---|---|
| p24+[(a)] | p24−[(b)] | p24+ | p24− |
| 114/159 | 105/107 | 159 | 107 |

[(a)] = p24 positive
[(b)] = p24 negative

We claim:

1. A peptide composition having specific immunoreactivity to antibodies to HTLV-III comprising a peptide with about 35 amino acids having an amino acid sequence:

Arg-Ile-Leu-Ala-Val-Glu-Arg-Tyr-Leu-Lys-Asp-Gln-Gln-Leu-Leu-Gly-Ile-Trp-Gly-Cys-Ser-Gly-Lys-Leu-Ile-Cys-Thr-Thr-Ala-Val-Pro-Trp-Asn-Ala-Ser , or analogues thereof, as long as the immunoreactivity to antibodies to HTLV-III derived from the three dimensional conformation is preserved substantially.

2. A peptide composition having specific immunoreactivity to antibodies to HTLV-III comprising a mixture of:

(i) about 10 to 95 parts by weight of a peptide of about twenty-one amino acids according to the formula: Arg-Ile-Leu-Ala-Val-Glu-Arg-Tyr-Leu-Asp-Gln-Gln-Leu-Leu-Gly-Ile-Trp-Gly-Cys-Ser, or analogues thereof; and (ii) about 5 to 90 parts by weight of a peptide of about nineteen amino acids according to the formula: Ile-Trp-Gly-Cys-Ser-Gly-Lys-Leu-Ile-Cys-Thr-Thr-Ala-Val-Pro-Trp-Asn-Ala-Ser, or analogues thereof, as long as the immunoreactivity of the analogues to antibodies to HTLV-III derived from the three dimensional conformation is preserved substantially.

3. A peptide composition according to claim 2 further comprising:

(iii) about 5 to 50 parts by weight of a peptide of about eleven amino acids according to the formula: Ile-Val-Arg-Met-Tyr-Ser-Pro-Thr-Ser-Ile-Leu, or analogues thereof, as long as the immunoreactivity to antibodies to HTLV-III is derived from the three dimensional conformation preserved substantially.

4. An immunoassay method for the detection of antibodies to HTLV-III and diagnosis of AIDS, ARC or pre-AIDS conditions comprising:

A. coating a solid support with an effective amount of the peptide composition according to claim 1 as an antigen;

B. adding a test sera diluted with a buffer wherein the antibodies to HTLV-III in the test sera form peptide-antibody complexes with the peptide composition;

C. incubating the mixture; and

D. detecting the presence of the peptide-antibody complexes.

5. An immunoassay method for the detection of antibodies to HTLV-III and diagnosis of AIDS, ARC or pre-AIDS conditions comprising:

A. coating a solid support with an effective amount of the peptide composition according to claim 2 as an antigen;

B. adding a test sera diluted with a buffer wherein the antibodies to HTLV-III in the test sera form peptide-antibody complexes with the peptide composition;

C. incubating the mixture; and

D. detecting the presence of the peptide-antibody complexes.

6. An immunoassay method for detection of antibodies to HTLV-III and diagnosis of AIDS, ARC, or pre-AIDS conditions comprising:

A. coating a solid support with an effective amount of the peptide composition according to claim 3 as an antigen;

B. adding a test sera diluted with a buffer wherein the antibodies to HTLV-III in the test sera form peptide-antibody complexes with the peptide composition;

C. incubating the mixture at room temperature; and

D. detecting the presence of the peptide-antibody complexes.

7. An immunoassay method according to claim 4 wherein step D. comprises: introducing a second antibody labelled with an enzyme and a substrate which reacts with the enzyme to form a colored product.

8. An immunoassay method according to claim 5 wherein step D. comprises: introducing a second antibody labelled with an enzyme and a substrate which reacts with the enzyme to form a colored product.

9. An immunoassay method according to claim 6 wherein step D. comprises: introducing a second antibody labelled with an enzyme and a substrate which reacts with the enzyme to form a colored product.

10. An immunoassay method according to claim 4 wherein step D. comprises: introducing a second known antibody labelled with a radioactive element.

11. An immunoassay method according to claim 5 wherein step D. comprises: introducing a second known antibody labelled with a radioactive element.

12. An immunoassay method according to claim 6 wherein step D. comprises: introducing a second known antibody labelled with a radioactive element.

13. An immunoassay method according to claim 7 wherein for each assay procedure, the amount of the peptide composition is about 1ug.

14. An immunoassay method according to claim 8 wherein for each assay procedure, the amount of the peptide composition is about 1ug.

15. An immunoassay method according to claim 9 wherein for each assay procedure, the amount of the peptide composition is about 1ug.

16. A peptide composition according to claim 2 wherein the mixture is 10 parts by weight of the peptide of about 21 amino acids: Arg-Ile-Leu-Ala-Val-Glu-Arg-Tyr-Leu-Lys-Asp-Gln-Gln-Leu-Leu-Gly-Ile-Trp-Gly-Cys-Ser and 1 part by weight of the peptide of about 19 amino acids: Ile-Trp-Gly-Cys-Ser-Gly-Lys-Leu-Ile-Cys-Thr-Thr-Ala-Val-Pro-Trp-Asn-Ala-Ser.

17. A peptide composition according to claim 3 wherein the mixture further comprises 1 part by weight of the peptide of about 11 amino acids: Ile-Val-Arg-Met-Tyr-Ser-Pro-Thr-Ser-Ile-Leu.

18. An immunoassay method for detection of antibodies to HTLV-III and diagnosis of AIDS, ARC or pre-AIDS conditions comprising:

A. coating a solid support with an effective amount of the peptide composition according to claim 16 as an antigen;

B. adding a test sera diluted with a buffer wherein the antibodies to HTLV-III in the test sera form peptide-antibody complexes with the peptide composition;

C. incubating the mixture at room temperature; and

D. detecting the presence of the peptide-antibody complexes.

19. An immunoassay method for detection of antibodies to HTLV-III and diagnosis of AIDS, ARC or pre-AIDS conditions comprising:

A. coating a solid support with an effective amount of the peptide composition according to claim 17 as an antigen;

B. adding a test sera diluted with a buffer wherein the antibodies to HTLV-III in the test sera form peptide-antibody complexes with the peptide composition;

C. incubating the mixture at room temperature; and

D. detecting the presence of the peptide-antibody complexes.

20. An immunoassay method according to claim 18 wherein step D. comprises: introducing a second antibody labelled with an enzyme and a substrate which reacts with the enzyme to form a colored product.

21. An immunoassay method according to claim 19 wherein step D. comprises: introducing a second antibody labelled with an enzyme and a substrate which reacts with the enzyme to form a colored product.

22. An immunoassay method according to claim 18 wherein step D. comprises: introducing a second known antibody labelled with a radioactive element.

23. An immunoassay method according to claim 19 wherein step D. comprises: introducing a second known antibody labelled with a radioactive element.

24. An immunoassay method according to claim 20 wherein for each assay procedure the amount of the peptide composition is about 1 ug.

25. An immunoassay method according to claim 21 wherein for each assay procedure the amount of the peptide composition is about 1 ug.

26. A test kit for the detection of antibodies to HTLV-III and the diagnosis of AIDS, ARC and pre-AIDS conditions comprising:

A. a solid support;

B. coating onto the solid support, an immunoadsorbent comprising a peptide composition according to claim 1 to form peptide-antibody complexes with antibodies to HTLV-III;

C. a sample of normal serum as negative control;

D. a sample of serum containing antibodies to HTLV-III as positive control; and

E. a buffer for diluting the serum samples.

27. A test kit for the detection of antibodies to HTLV-III and the diagnosis of AIDS, ARC and pre-AIDS conditions comprising:

A. a solid support;

B. coating onto the solid support, an immunoadsorbent comprising a peptide composition according to claim 2 to form peptide-antibody complexes with antibodies to HTLV-III;

C. a sample of normal serum as negative control;

D. a sample of serum containing antibodies to HTLV-III as positive control; and

E. a buffer for diluting the serum samples.

28. A test kit for the detection of antibodies to HTLV-III and the diagnosis of AIDS, ARC and pre-AIDS conditions comprising:

A. a solid support;

B. coating onto the solid support, an immunoadsorbent comprising a peptide composition according to claim 3 to form peptide-antibody complexes with antibodies to HTLV-III;

C. a sample of normal serum as negative control;

D. a sample of serum containing antibodies to HTLV-III as positive control; and

E. a buffer for diluting the serum samples.

29. A test kit for the detection of antibodies to HTLV-III and the diagnosis of AIDS, ARC and pre-AIDS conditions comprising:

A. a solid support;

B. coating onto the solid support, an immunoadsorbent comprising a peptide composition according to claim 16 to form peptide-antibody complexes with antibodies to HTLV-III;

C. a sample of normal serum as negative control;

D. a sample of serum containing antibodies to HTLV-III as positive control; and

E. a buffer for diluting the serum samples.

30. A test kit for the detection of antibodies to HTLV-III and the diagnosis of AIDS, ARC and pre-AIDS conditions comprising:

A. a solid support;

B. coating onto the solid support, an immunoadsorbent comprising a peptide composition according to claim 17 to form peptide-antibody complexes with antibodies to HTLV-III;

C. a sample of normal serum as negative control;

D. a sample of serum containing antibodies to HTLV-III as positive control; and

E. a buffer for diluting the serum samples.

31. A test kit according to claim 26 further comprising:

F. an enzyme labelled second antibody for binding with the formed peptide-antibody complexes;

G. a substrate which reacts with the enzyme labelled antibody to form a colored product; and H. a second buffer solution for stopping the further development of the colored product.

32. A test kit according to claim 27 further comprising:

F. an enzyme labelled second antibody for binding with the formed peptide-antibody complexes;

G. a substrate which reacts with the enzyme labelled antibody to form a colored product; and H. a second buffer solution for stopping the further development of the colored product.

33. A test kit according to claim 28 further comprising:

F. an enzyme labelled second antibody for binding with the formed peptide-antibody complexes;

G. a substrate which reacts with the enzyme labelled antibody to form a colored product; and H. a second buffer solution for stopping the further development of the colored product.

34. A test kit according to claim 29 further comprising:

F. an enzyme labelled second antibody for binding with the formed peptide-antibody complexes;

G. a substrate which reacts with the enzyme labelled antibody to form a colored product; and H. a second buffer solution for stopping the further development of the colored product.

35. A test kit according to claim 30 further comprising:

F. an enzyme labelled second antibody for binding with the formed peptide-antibody complexes;

G. a substrate which reacts with the enzyme labelled antibody to form a colored product; and H. a second buffer solution for stopping the further development of the colored product.

36. A test kit according to claim 26 further comprising:

F. a radioactive element labelled second antibody for binding with the formed peptide-antibody complexes to detect the peptide-antibody complexes.

37. A test kit according to claim 27 further comprising:

F. a radioactive element labelled second antibody for binding with the formed peptide-antibody complexes to detect the peptide-antibody complexes.

38. A test kit according to claim 28 further comprising:

F. a radioactive element labelled second antibody for binding with the formed peptide-antibody complexes to detect the peptide-antibody complexes.

39. A test kit according to claim 29 further comprising:

F. a radioactive element labelled second antibody for binding with the formed peptide-antibody complexes to detect the peptide-antibody complexes.

40. A test kit according to claim 30 further comprising:

F. a radioactive element labelled second antibody for binding with the formed peptide-antibody complexes to detect the peptide-antibody complexes.

41. A peptide composition having specific immunoreactivity to antibodies to HTLV-III comprising a peptide with about 19 amino acids having an amino acid sequence:

Ile-Trp-Gly-Cys-Ser-Gly-Lys-Leu-Ile-Cys-Thr-Thr-Ala-Val-Pro-Trp-Asn-Ala-Ser, or analogues thereof as long as the immunoreactivity of the analogues to antibodies HTLV-III derived from the three dimensional conformation is substantially preserved.

42. A peptide composition having specific immunoreactivity to antibodies to HTLV-III comprising a peptide with about 11 amino acids having an amino acid sequence:

Ile-Val-Arg-Met-Tyr-Ser-Pro-Thr-Sev-Ile-Leu or analogues thereof, as long as the immunoreactivity to antibodies to HTLV-III derived from the three dimensional conformation is substantially preserved.

43. An immune assay method for the detection of antibodies to HTLV-III and diagnosis of AIDS, ARC or pre-AIDS conditions comprising:

A. coating a solid support with an effective amount of the peptide composition according to claim 41 as an antigen;

B. adding a test sera diluted with a buffer wherein the antibodies to HTLV-III in the test sera form peptide-antibody complexes with the peptide composition;

C. incubating the mixture; and

D. detecting the presence of the peptide-antibody complexes.

44. An immune assay method for the detection of antibodies to HTLV-III and diagnosis of AIDS, ARC or pre-AIDS conditions comprising:

A. coating a solid support with an effective amount of the peptide composition according to claim 42 as an antigen;

B. adding a test sera diluted with a buffer wherein the antibodies to HTLV-III in the test sera form peptide-antibody complexes with the peptide composition;

C. incubating the mixture; and

D. detecting the presence of the peptide-antibody complexes.

45. An immunoassay method according to claim 43 wherein step D. comprises: introducing a second antibody labelled with an enzyme and a substrate which reacts with the enzyme to form a colored product.

46. An immunoassay method according to claim 44 wherein step D. comprises: introducing a second antibody labelled with an enzyme and a substrate which reacts with the enzyme to form a colored product.

47. An immunoassay method according to claim 43 wherein step D. comprised introducing a second known antibody labelled with a radioactive element.

48. An immunoassay method according to claim 44 wherein step D. comprised introducing a second known antibody labelled with a radioactive element.

49. An immunoassay method according to claim 45 wherein for each assay procedure, the amount of the peptide composition is about 1 ug.

50. An immunoassay method according to claim 48 wherein for each assay procedure, the amount of the peptide composition is about 1 ug.

51. A test kit for the detection of antibodies to HTLV-III and the diagnosis of AIDS, ARC and pre-AIDS conditions comprise:

A. a solid support;

B. coating onto the solid support, in immunoadsolvent comprising a peptide composition according to claim 41 to peptide-antibody complexes with antibodies to HTLV-III;

C. a sample of normal serum as negative control;

D. a sample of serum containing antibodies to HTLV-III as positive control; and

E. a buffer for diluting the serum samples.

52. A test kit for the detection of antibodies to HTLV-III and the diagnosis of AIDS, ARC and pre-AIDS conditions comprise:

A. a solid support;

B. coating onto the solid support, in immunoadsolvent comprising a peptide composition according to claim 42 to peptide-antibody complexes with antibodies to HTLV-III;

C. a sample of normal serum as negative control;

D. a sample of serum containing antibodies to HTLV-III as positive control; and

E. a buffer for diluting the serum samples.

* * * * *